(12) United States Patent
Piasio et al.

(10) Patent No.: US 7,718,375 B2
(45) Date of Patent: May 18, 2010

(54) MODIFICATION OF BIOASSAYS FOR DETECTION OF ANTIGENS CHARACTERISTIC OF BACTERIA THAT ARE CAUSATIVE OF EAR AND RESPIRATORY INFECTIONS TO ELIMINATE FALSE POSITIVE RESULTS CAUSED BY NASOPHARYNGEAL COLONIZATION OF CHILDREN

(75) Inventors: Roger N. Piasio, Cumberland Foreside, ME (US); Madeline Wareing, Cape Elisabeth, ME (US)

(73) Assignee: Binax, Inc., Portland, ME (US)

( * ) Notice: Subject to any disclaimer, the term of this patent is extended or adjusted under 35 U.S.C. 154(b) by 36 days.

(21) Appl. No.: 10/083,476

(22) Filed: Feb. 27, 2002

(65) Prior Publication Data

US 2005/0260694 A1 Nov. 24, 2005

(51) Int. Cl.
*G01N 33/53* (2006.01)
*G01N 33/569* (2006.01)
(52) U.S. Cl. ...................... 435/7.1; 435/7.34
(58) Field of Classification Search .............. 435/7.1, 435/7.2, 7.34, 970, 971, 7.54; 530/413, 417; 436/413, 417
See application file for complete search history.

(56) References Cited

U.S. PATENT DOCUMENTS

| | | | |
|---|---|---|---|
| 4,806,312 A | 2/1989 | Greenquist | 422/56 |
| 4,959,305 A | 9/1990 | Woodrum | 435/7.7 |
| 5,451,504 A | 9/1995 | Fitzpatrick et al. | 435/7.2 |
| 6,824,997 B1 * | 11/2004 | Moore et al. | 435/7.34 |

FOREIGN PATENT DOCUMENTS

WO   WO 89/05978   6/1989

OTHER PUBLICATIONS

Adegbola et al. Pediatr. Infect. Dis. J. 20: 718-719, Jul. 2001.*
Dowell et al. Clin. Infect. Dis. 32: 824-825, 2001.*
Navarro et al. J. Clin. Microbiol. 42: 4853-4855, 2004—abstract.*
Niriai et al. Kansenshogaku Zasshi 78: 18-21, Jan. 2004—abstract.*
Dominguez et al. J. Clin. Microbiol. 41: 2161-2163, May 2003—abstract.*
Hamer et al. Clin. Infect. Dis. 61: 1025-1028, Apr. 2002.*
Magentie et al. Ann. Biol. Clin. 61: 106-109, Jan.-Feb. 2003—abstract.*

* cited by examiner

Primary Examiner—S. Devi

(57) ABSTRACT

The present invention relates to modifying rapid immunochromatographic ("ICT") tests for the detection of characteristic carbohydrate antigens of bacteria that are known to be causative of otitis media and respiratory diseases in children under the age of approximately 12 years. The test modifications involve either (1) reducing the total amount of antibodies to the carbohydrate antigen employed in each test, (2) adding at least one fixed "scrub" line located just prior to the capture line in the sample flow path to the prepared ICT test strip to "scrub" out an identical amount of target antigen from all bodily fluid test samples obtained from both colonized but otherwise healthy children and diseased children, or (3) combinations of (1) and (2).

1 Claim, No Drawings

MODIFICATION OF BIOASSAYS FOR DETECTION OF ANTIGENS CHARACTERISTIC OF BACTERIA THAT ARE CAUSATIVE OF EAR AND RESPIRATORY INFECTIONS TO ELIMINATE FALSE POSITIVE RESULTS CAUSED BY NASOPHARYNGEAL COLONIZATION OF CHILDREN

The present invention relates to the modification of rapid tests, such as immunochromatographic tests, presently used to diagnose such diseases as otitis media and pneumococcal pneumonia, to reduce the incidence in children particularly of false positive results attributable to nasopharyngeal colonization of otherwise healthy individuals by the same bacteria that are responsible for otitis media and either pneumococcal pneumonia, to reduce the incidence in children particularly of false positive results attributable to nasopharyngeal colonization of otherwise healthy individuals by the same bacteria that are responsible for otitis media and either pneumococcal pneumonia per se or pneumonic diseases clinically indistinguishable therefrom.

BACKGROUND OF THE INVENTION

Pneumonic disease and otitis media, especially in children up to the age of about 12 years, represent a serious global health problem which is aggravated by the ever-growing ability of bacteria to mutate into forms that are increasingly resistant to the therapeutic effect of the various antibiotics which are the most effective medications against them. In the United States alone, approximately 4.3 million cases of pneumonia occur in persons of all ages annually and about half of them are caused by bacteria. About 2.5 million visits to physicians are made in the U.S. for the purpose of seeking treatments for otitis media—again about 50% attributable to bacteria. Otitis media is known to be largely a disease of young children.

It has been estimated that about 4 million children throughout the world die annually from acute respiratory diseases, preponderantly in developing countries. Studies show that *Streptococcus pneumoniae* is the leading cause of bacterial pneumonia in developing countries and a major cause of child mortality.

All of these problems have been complicated by the fact that accurate diagnosis of bacterially caused respiratory infection, and acute ear infection (i.e., otitis media) in children was slow and difficult until recently. It has been known for some years that bacterial antigens were present in bodily fluids of persons infected with pneumococcal pneumonia, such as e.g., blood, sputum, urine, etc., but until recently there was little progress in using this knowledge as the basis for developing a reliable test for such antigens. In the meantime, the standard for accurate diagnosis of pneumococcal pneumonia and other *Streptococcus pneumoniae*—caused diseases has been a bacterial culture test which usually required some days to complete and had other considerable drawbacks, such e.g., as the difficulty of obtaining a suitable sample for culturing and the drawback of having to medicate the patient while awaiting the culture test outcome with a broad spectrum antibiotic, all of which drawbacks are well documented in the medical literature.

In 1999, the United States Food and Drug Administration approved a rapid (i.e. about 20 minutes) immunochromatographic ("ICT") bioassay for the detection of *Streptococcus pneumoniae* in bodily fluids, particularly urine. This test, which is commercially available from Applicants' assignee under the trademark NOW®, detects the C-polysaccharide antigen which is present in all serotypes of *Streptococcus pneumoniae*. In adults and most teenagers, the test has a sensitivity of 78% for pneumococcal pneumonia infections and 82-86% for bacteremic forms thereof and a specificity of over 95%. See Dominguez, J., Gali, N. Blanco, S. et al, Detection of *Streptococcus pneumoniae* antigen by a rapid immunochromatographic assay in urine, Chest 2001, vol. 119, 243-9; Yu V. L., Kellog, J. A, Plouffe, J. F. et al, Evaluation of the Binax Urinary, Gram stain and sputum culture for *Streptococcus pneumoniae* in patients with community-acquired pneumonia, 38th Annual Meeting of the Infectious Disease Society of America, New Orleans, La., Abstract #262 (2001).

The NOW® bioassay is described and claimed in co-pending, commonly assigned U.S. patent application Ser. No. 09/399,710 filed Sep. 16, 1999, and also its parent application Ser. No. 09/156,486 filed Sep. 18, 1998 and now abandoned.

A study of pneumonia conducted in China found that children with nasopharyngeal carriage of *Streptococcus pneumoniae* had high rates of positive urine results in the NOW® test even when they had no pneumonic disease and that the test results accordingly did not fit the sensitivity and specificity profile established with adult subjects. A study in Gambia found that 87% of well children tested were nasopharyngeal carriers of *Streptococcus pneumoniae* and that 55% of these, or about 47% of this population, gave false positive results in the Binax NOW® test. See Adegbola, R. A., Obaro, S. K., Biney, E. and Greenwood, B. M., Evaluation of Binax NOW® *Streptococcus pneumoniae* urinary antigen test in children in a community with a high carriage rate of pneumococcus, Pediatr. Infect. Dis. J. 2001, July; 20 (7) 718-719. See also Dowell, S. F., Garman, R. L., Liu, G., Levine, O. S. and Yang, Y. H., Evaluation of Binax NOW® as assay for the detection of pneumococcal antigen in urine samples performed among pediatric patients, Clin Infect Dis. J. 2001, vol. 32, 824-825 (2001). A similar study conducted among 210 children in Quito, Ecuador, confirmed that urine from children with nasopharyngeal carriage of *Streptococcus pneumoniae* gives a high proportion of false positive results in the Binax NOW® test. See Hamer, D., Egas. J., Estrella, B., MacLeod MacLood, W. et al, 2002. An assessment of the Binax NOW® *Streptococcus Pneumoniae* urinary test in children with Nasopharyngeal pneumococcal colonization, (Publication in press).

An article reviewing published studies performed on Scandinavian and Israeli children confirms that young children in these areas have a high rate of nasopharyngeal colonization, not only of *Streptococcus pnuemoniae* but also of the bacteria that are known to cause disease states that resemble pneumococcal pneumonia, including especially non-typable *Haemophilus influenzae* and *Moraxella catarrhalis* which, with *Streptococcus pneumoniae*, are the most common causes of otitis media. Among other agents that tend to colonize the nasopharynx and are causatives of both pneumonic illness clinically very similar to pneumococcal pneumonia and otitis media are *Staphylococcus aureus*, a number of other bacteria and some viruses. See Harper, M. B., Nasopharyngeal colonization with pathogens causing otitis media; how does this information help us? Pediatr Infec. Dis. J. vol. 18, 1120-1124 (1999).

Copending, commonly assigned U.S. application Ser. No. 09/518,165 filed Mar. 1, 2002, describes and claims rapid immunochromatographic tests for detecting bacterial carbohydrate antigens in human bodily fluids, including urine.

The methodology for lessening and/or eliminating false positives in child carriers who are colonized nasopharyngeally as described herein is applicable to the modification of tests for antigens of other bacteria which tests are disclosed in copending, commonly assigned application Ser. No. 09/518, 165 as well as to the test for *Streptococcus pneumoniae* antigens described in commonly assigned application Ser. No. 09/397,110, now U.S. Pat. No. 6,824,997.

In general, the development of rapid, reliable, specific and sensitive assays for antigens of bacteria causative of common respiratory tract and ear infections in children—and especially pneumonia and otitis media because of their high incidence—is important to complement the strategies that the Centers for Disease Control in the United States and the World Health Organization globally have formulated for decelerating the pace of development by causative bacteria of strains resistant to antibiotic therapy.

BRIEF DESCRIPTION OF THE INVENTION

The present invention involves modifying of the Binax NOW® immunochromatographic ("ICT") antigen test for use with young children, especially in geographic areas where nasopharyngeal colonization of these children with *Streptococcus pneumoniae* is a significant clinical manifestation, to markedly diminish or eliminate false positive test results that have been obtained when testing the urine of non-diseased children who are nasopharyngeal carriers of *Streptococcus pneumoniae*. The invention encompasses making analogous modifications of other immunoassay rests for other antigens characteristic of *Streptococcus pneumoniae* and antigens characteristic of other bacteria that both (1) are causative of pneumonic disease and otitis media in young children and (2) tend to colonize the nasopharynx in uninfected children.

The test modifications rest upon the unexpected discovery that, in general, nasopharyngeal carriage of disease-causing bacteria results in lower concentrations in bodily fluids, including urine, of target bacterial antigens for the ICT tests described in earlier filed, patent application U.S. Ser. No. 09/397,110, now U.S. Pat. No. 6,824,997 and U.S. Ser. No. 09/518,165, than the concentrations of the same antigens found in bodily fluids of children infected with pneumonic disease or otitis media.

The modified tests employ reduced concentrations of antibodies to the target bacterial antigens.

The objective of the modifications, which is to maintain high specificity for diseased patient samples and to improve sensitivity to those samples by screening out samples from healthy, but nasopharyngeally colonized, children which gave false positives in the standard NOW® test for *Streptococcus pneumoniae*.

DETAILED DESCRIPTION OF THE INVENTION

The NOW® bioassay for identifying the characteristic C-polysaccharide antigen of *Streptococcus pneumoniae* present in all serotypes of these bacteria, has been demonstrated to be highly satisfactory in enabling physicians to make rapid, accurate diagnoses of a variety of *Streptococcus pneumoniae*—caused disease states in adults by coordinating carefully observed clinical symptoms with the test results. This ICT test is described and claimed in commonly assigned, U.S. patent application Ser. No. 09/397,110, now U.S. Pat. No. 6,824,997. U.S. application Ser. No. 09/518,165, also and commonly assigned, discloses how to construct and perform analogous ICT bioassays which target characteristic carbohydrate antigens of other bacteria, including but by no means limited to non-typable *Haemophilus influenzae*, *Moraxella catarrhalis*, and *Staphylococcus aureus*.

The modifications disclosed herein of the NOW® test disclosed and claimed in U.S. Pat. No. 6,824,997 render the test as so modified highly useful in enabling physicians to make rapid, accurate diagnoses of pneumococcal pneumonia and/or otitis media caused by *Streptococcus pneumoniae* in children, which diagnoses are based on the modified test results combined with clinical observations of the individual patients. Analogous modifications of the tests covered in U.S. Ser. No. 09/518,165 render those tests as so modified very useful in enabling physicians to make rapid, accurate diagnoses of pneumonic diseases and otitis media of other bacterial origin in children, by combining the modified test results with clinical observation of individual child patients. Similar modifications may be made to any bioassay for an antigen characteristic of bacteria that tend to colonize nasopharyngeally in children and are causatives of pneumonic disease and/or otitis media, in order to improve diagnostic reliability on the assay results by diminishing or eliminating false positive results in children due to nasopharyngeal colonization.

To put the specific modified tests described in the examples of this application in perspective, a brief summary of the bioassay format described in both of the prior copending applications is provided. Succinctly, antibodies to the target bacteria are obtained by conventionally injecting a laboratory animal with the bacteria and conventionally obtaining from the animal a blood sample containing antibodies to the injected bacteria after a suitable time interval. Meanwhile, there is obtained from a culture of the same bacteria by a purification process described in the copending applications, an essentially protein-free carbohydrate antigen characteristic of these bacteria. The thus-purified antigen is coupled to a chromatographic column and the antibodies from the animal are rendered antigen-specific by passing them over the antigen coupled to the column. The antibodies as so purified and rendered antigen-specific are in part conjugated to a label, such as colloidal gold, and in part placed in an aqueous buffered dilute sucrose solution at a specified antibody concentration level. Each ICT bioassay comprises the use of a strip of bibulous material in a housing. The strip has a sample receiving zone at one end, a deposit of tagged purified antibody conjugate located immediately ahead of the sample receiving zone, which deposit is rendered flowable by contact with liquid sample, a region through which sample and tagged purified antibodies flow laterally together, a capture zone comprising an immovable bound stripe of purified antibodies deposited thereon from buffered dilute sucrose solution, an upstream control line and by an absorption pad which absorbs the liquid sample and any excess tagged antibodies. The capture zone is equipped with a view window in the device which allows the test operator to see color changes developed along the capture line and the control line. When the test is run and the target bacterial antigen is present in the liquid sample, after the sample is applied to the strip and picks up the tagged antibodies as it flows along, conjugates of tagged antibody and target antigen form during further flow to the capture line, where tagged antibody-target antigen-fixed antibody "sandwiches" form and become visible as a result of the massing of tag along the fixed capture line.

According to the present invention, the test is modified for children to screen out otherwise positive tests of nasopharyngeal carriers of bacteria containing the target antigen by varying the concentration of tagged purified antibody movably deposited on the test strip and the concentration of purified antibody fixedly placed on the strip to form the fixed capture line.

It is noted that the nasopharyngeal colonization of children is said in the literature to decrease with increasing age of the children. By about age 12 and in many cases earlier, the problem has disappeared and the problem of false positives has likewise essentially disappeared.

In approaching the problem of false positives obtained in using the NOW® test on samples from nasopharyngeally colonized child carriers of Streptococcus pneumoniae, 210 individual samples of urine were obtained from the Ecuadorian study described by the Hamer et al article cited above. These samples were preliminarily divided into three groups based on information that accompanied them as received.

1. Samples that had tested negative in a bacterial culture test and also in the NOW® test, all of which were labelled NEGATIVE.

2. Samples that had tested positive in the same bacterial culture test and also in the NOW® test, all of which were labelled POSITIVE.

3. Samples which had tested negative in the same culture test but had tested positive in the NOW® test, which were labeled CARRIER.

The objective of the experimental work thereupon performed was to modify the NOW® test in such a way as to reduce markedly or wholly eliminate the positive CARRIER results, thus increasing sensitivity of the test to pneumococcal pneumonia and otitis media disease states caused by Streptococcus pneumoniae while maintaining the specificity of the test at no less than the 90% level and preferably better.

Randomly selected samples from the groups 2 and 3 of the Ecuadorian childrens' urine samples described above were used to conduct the tests described in the following examples.

In all of these examples, test strips were prepared as described in earlier filed, application Ser. No. 09/397,110, now U.S. Pat. No. 6,824,997 using antibodies to Streptococcus pneumoniae that had been purified and rendered antigen-specific as described in that application. In all of these tests, the capture lines were striped on the test strip membranes by passing each of them under the delivery tip of a precision pump system at a rate of 0.5 ml. per 6 mm. of membrane.

Example 1

Reducing Capture Line Concentration Only

In this example, the concentration of the capture line was reduced from the 1.25 mg./ml. normally used to each of the concentrations shown in the table. The optical density of the gold-purified antibody conjugate which is indicative of concentration, was maintained a 2.0 The test results appear in Table 1:

TABLE I

| Antibody Concentration of Capture Line | Carriers Giving Negative Result | Samples POSITIVES % Positive |
| --- | --- | --- |
| 0.3 mg./ml. | 1 of 7 = 14% samples | 100% |
| 0.5 mg./ml. | 4 of 11 = 36% samples | 100% |
| 1.0 mg./ml. | 1 of 11 = 9% samples | 100% |

These results show that reducing capture line concentration alone to 0.3 mg./ml. had no significant effect on elimination of false positive results in the carrier samples. It was decided to run further tests with varying capture line antibody concentrations below 0.5 mg./ml.

Example 2

Reducing Both Capture Line Concentration and Conjugate Concentration

In this Example, the test conjugate concentration was reduced approximately 25% from an optical density of 2.0 to an optical density value of 1.5 for all samples run, and the capture line concentrations were as shown in Table II:

TABLE II

| Antibody Concentration of Capture Line | Carriers Giving Negative Result | POSITIVES % Positive |
| --- | --- | --- |
| 0.1 mg./ml. | 1 of 6 = 17% samples | 66% |
| 0.2 mg./ml. | 9 of 13 = 69% samples | 100% |
| 0.3 mg./ml. | 10 of 14 = 72% samples | 100% |
| 0.4 mg./ml. | 7 of 14% = 50% samples | 100% |

These results show that the specificity of the test declined when a capture line concentration as low as 0.1 mg./ml. was employed. However, with the reduced optical density (i.e. conjugate concentration) in all tests, it was calculated that sensitivity of the test to disease states due to elimination of false positives increased to more than 90% with a capture line concentration of 0.3 mg./ml., while the tests at these capture line and conjugate concentrations made on Positive samples were all positive, indicating specificity of the test was unaffected. Raising the capture line concentrations to 0.4 mg./ml. decreased sensitivity by raising the proportion of false positives. It was also noted that the 0.1 mg./ml. capture line concentration reduced the ability of the test to detect Positive samples from diseased children and had little effect on reducing false positives.

Example 3

Reducing Conjugate and Capture Line Concentrations and Adding a Scrub Line

Using conjugate of optical density 1.5 and a capture line concentration of 1.0 mg./ml. in all tests, the addition of a "scrub" line of varying concentration was tested on a number of samples, as shown in Table III. The scrub line was experimented with to see if by "scrubbing" out a portion of the antigen present in both the carrier samples and the Positive samples, which generally have significantly higher antigen levels than the carrier samples, the sensitivity of the test toward disease detection could be increased without any major effect on test specificity.

For the test strips used in these tests, the scrub line was positioned 0.3 milliliters ahead of the capture line in the flow path. Each sample/tagged antibody mixture first flowed over the scrub line and then reached the capture line after "scrubbing".

TABLE III

| Scrub Line Antibody Concentration | Carriers Giving Negative Result | POSITIVES |
| --- | --- | --- |
| 0.3 mg./ml. | 22 of 35 = 63% samples | 7 of 8 = 87.5% samples |
| 0.4 mg./ml. | 19 of 35 = 54% samples | 5 of 6 = 83% samples |
| 0.5 mg./ml. | 18 of 29 = 62% samples | 5 of 8 = 62.5% samples |
| 0.6 mg./ml. | 21 of 29 = 72% samples | 4 of 8 = 50% samples |

While these tests generally showed increasing elimination of false positives with increasing concentration of the scrub line, the specificity of the test was adversely affected. Moreover, increasing the concentration of the scrub line did not remove all antigen from of the false positive samples and it was therefore decided to try multiple scrub lines, each of lower concentration than the 0.3 mg./ml. scrub line used in one series of tests in this Example.

Example 4

Reduced Concentration of Capture Line and Conjugate with Multiple Scrub Lines

In this series of test runs, the capture line was maintained at a concentration of 1.0>mg./ml. throughout while the conjugate concentration was held at that producing an optical density of 1.5. The number of scrub lines and concentration of each line is each test series in shown in Table IV. The scrub lines were separately striped on ahead of the capture line in the flow path, with the first one being 2 mm ahead, the second one 4 mm. ahead and the third one, 6 mm. ahead. In each test series, the 2 or 3 scrub lines employed in that series had identical antibody concentrations.

TABLE IV

| No.# of Scrub Lines | Antibody Concentration of Each Scrub Line | Carriers Testing Negative | Positive (% Positive) |
| --- | --- | --- | --- |
| 2 | 0.1 mg./ml. | 4 of 11 = 36% samples | 10 of 11 = 91% samples |
| 2 | 0.15 mg./ml. | 5 of 9 = 55% samples | 3 of 5 = 60% samples |
| 2 | 0.2 mg./ml. | 5 of 10 = 50% samples | 3 of 5 = 60% samples |
| 2 | 0.25 mg./ml. | 7 of 11 = 82% samples | 7 of 11 = 70% samples |
| 3 | 0.1 mg./ml. | 10 of 10 = 100% samples | 1 of 5 = 20% samples |

While the test series using 3 scrub lines of 0.1 mg./ml. antibody concentration was effective in wholly eliminating false positives it also eliminated 80% of the Positive samples. Putting aside the 3-scrub line test series, the results in the table reflect that the amount of antigen removed from the Positive samples in those series with 2 scrub lines, each having an antibody concentration above 0.1 mg./ml. adversely affected the test results on Positive samples, decreasing specificity and sensitivity.

It is intended to run further tests using two and three scrub lines at lower concentrations than were incorporated in this series, to try to eliminate false positives without adversely affecting the sensitivity and specificity of the test toward diseased patient's samples. It is also intended to try combinations of 1-3 scrub lines with the capture line concentration and the optical density maintained at the level currently used for the NOW® test on the premise that scrubbing out the level of antigen in the sample in the urine of most carriers prior to the capture line in both carrier and positive samples may leave a sufficient antigen level in the urines of diseased patients to be detected at capture line of higher antibody concentration. In this regard, it is important to recognize that the lack of any statistically significant figures showing the level of antigen in the urine of humans infected with *Streptococcus pneumoniae* versus the level of antigen in urine of healthy children nasopharyngeally colonized with *Streptococcus pneumoniae* makes it necessary to proceed empirically in establishing how to screen healthy carriers of bacteria known to be causative of otitis media and pneumococcal diseases from actually diseased children. The medically recognized dangers in medicating otherwise healthy carrier children with antibiotics based on false positive test results render it urgent that this work, empirical though it be, continue forward rapidly.

Further test series on urines from other populations of children including nasopharyngeal carriers are planned with variations in other test parameters.

From the tests to date, the ultimate objective of maintaining test specificity at 90% or better and increasing sensitivity of the test to diseased children while eliminating or at least minimizing false positives due to nasopharyngeal colonization (i.e. carriers) is clearly achievable by several routes, all involving reduced conjugate concentration and reduced capture line antibody concentration in comparison to the concentrations employed in the NOW® test for adults. Some of them, involving the introduction of at least one scrub line positioned prior to the capture line in the sample flow path of the test devices are believed to be capable of being combined with the present concentrations of antibodies on the capture line and in the conjugate that are used in the NOW® test. Inasmuch as those skilled in the art of immunology will readily conceive of permutations and combinations of variables that will be successful, it is intended that the invention as disclosed be limited only insofar as the appended claims may require.

It is also clear that other immunoassays for antigens characteristic of bacteria that colonize the nasopharynx area of children and are causative of pneumococcal and ear infections in children may be modified for use in children so as to increase the diagnostic reliability of the assay by reducing substantially, or eliminating, false positive results by either reducing the overall concentration of antibodies used in the specific assay or combining concentration levels in use in tests designed for the adult population with one or more "scrub" lines. In either case modifications will be arrived at by applying study techniques analogous to those used herein to arrive at specific limits—and for that reason also, this invention is limited only by the appended claims.

We claim:

1. A method for detecting a symptomatic *Streptococcus pneumoniae* infection in a human subject of age 12 years or less comprising:
    applying, to a sample receiving zone at an end of a bibulous test strip, a urine sample obtained from the human subject of age 12 years or less;
    allowing the urine sample to flow laterally along the bibulous test strip;
    mobilizing tagged purified antibodies capable of binding the C-polysaccharide antigen of *Streptococcus pneumoniae*, the tagged purified antibodies having been present immediately ahead of the sample receiving zone on the bibulous test strip and rendered flowable by contact with the urine sample, to form a mixture comprising the urine sample and the mobilized tagged purified antibodies;

allowing the binding of the tagged purified antibodies and the C-polysaccharide antigen, to form conjugates of the tagged purified antibodies and the C-polysaccharide antigen in the mixture;

allowing the mixture comprising the conjugates of the tagged purified antibodies and the C-polysaccharide antigen to flow further along the bibulous test strip;

allowing the binding of the conjugates of the tagged purified antibodies and the C-polysaccharide antigen to scrub line antibodies specific for the conjugates of the tagged purified antibodies and the C-polysaccharide antigen, the scrub line antibodies having been immobilized in at least one scrub line along the bibulous test strip;

allowing the mixture comprising the conjugates of the tagged purified antibodies and the C-polysaccharide antigen to flow downstream of the at least one scrub line; and allowing the binding of capture line antibodies specific for the conjugates of the tagged purified antibodies and the C-polysaccharide antigen, the capture line antibodies having been immobilized in a capture line downstream of the at least one scrub line, to the conjugates of the tagged purified antibodies and the C-polysaccharide antigen, wherein color formation in the downstream capture line resulting from the binding of the conjugates of the tagged purified antibodies and the C-polysaccharide antigen to the immobilized capture line antibodies specific for the conjugates of the tagged purified antibodies and the C-polysaccharide antigen is indicative of the symptomatic *Streptococcus pneumoniae* infection in the subject.

* * * * *